United States Patent [19]

Asanuma et al.

[11] 4,176,156
[45] Nov. 27, 1979

[54] METHOD FOR HEAT-STERILIZING ARTIFICIAL KIDNEYS

[75] Inventors: Akira Asanuma; Nobuo Taneda; Ryozo Hasegawa; Shohei Jindai; Toshio Morishita, all of Iwakuni, Japan

[73] Assignee: Teijin Limited, Osaka, Japan

[21] Appl. No.: 847,619

[22] Filed: Nov. 1, 1977

[30] Foreign Application Priority Data

Nov. 5, 1976 [JP] Japan .................. 51-132301
Nov. 9, 1976 [JP] Japan .................. 51-133738
Nov. 9, 1976 [JP] Japan .................. 51-133739
May 25, 1977 [JP] Japan .................. 52-66284[U]
May 26, 1977 [JP] Japan .................. 52-66912[U]

[51] Int. Cl.$^2$ .................. A61M 1/03; A61L 1/00
[52] U.S. Cl. .................. 422/25; 210/321 B; 422/26; 422/44
[58] Field of Search .................. 21/56, 2, 99, 78; 23/258.5 R, 258.5 M; 422/25, 26, 44

[56] References Cited

U.S. PATENT DOCUMENTS

| | | | |
|---|---|---|---|
| 3,016,284 | 1/1962 | Trexler | 21/2 |
| 3,099,519 | 7/1963 | Falkenblad et al. | 21/2 |
| 3,481,691 | 12/1969 | Trainham | 21/56 X |
| 3,691,068 | 9/1972 | Cross | 210/22 |
| 3,948,601 | 4/1976 | Fraser et al. | 23/258.5 R X |

FOREIGN PATENT DOCUMENTS

1482071 8/1977 United Kingdom .

*Primary Examiner*—Barry S. Richman
*Attorney, Agent, or Firm*—Wenderoth, Lind & Ponack

[57] ABSTRACT

A method for heat sterilizing an artificial kidney comprising a receptacle having accommodated therein permselective hollow filaments and including inlet and outlet ports for the blood and inlet and outlet ports for a dialyzate, which comprises (a) filling a primer consisting of water or a water solution into the artificial kidney,
(b) connecting a pressure buffer tank to at least one of the inlet and outlet ports,
(c) sealing the remaining ports by stopper means,
(d) heating the artificial kidney to a temperature of 80° to 130° C. to heat sterilize it, and moving the gas and a part of the primer in the artificial kidney which have been expanded by heating to the pressure buffer tank,
(e) cooling the artificial kidney to return the primer in the buffer tank to the artificial kidney, and
(f) aseptically sealing the port connected to the pressure buffer tank; and artificial kidneys of specified constituent elements suitable for use in heat sterilization by this method.

10 Claims, 9 Drawing Figures

METHOD FOR HEAT-STERILIZING ARTIFICIAL KIDNEYS

BACKGROUND OF THE INVENTION

This invention relates to a novel method for heat-sterilizing artificial kidneys, and to artificial kidneys suitable for use in heat sterilization by this method.

An artificial kidney is already known which includes a receptacle having accommodated therein permselective hollow flaments and comprising blood inlet and outlet ports and dialyzate inlet and outlet ports. The artificial kidney performs the function of kidneys of the living body by the removal of wastes from the blood into the dialyzate and the ultrafiltration of excess water in the blood. The importance of hollow filaments-containing artificial kidneys has increased rapidly because of their small sizes for the available membrane area and their ease of use.

It is necessary to sterilize artificial kidneys during production so as to avoid microbial contamination, and to supply them in the microbe-free state to the users. The users perform a necessary pretreatment on the sterilized artificial kidneys prior to use.

In the past, pre-use sterilization of artificial kidneys has been performed mainly by the following two typical methods.

According to one method, the manufacturers sterilize the artificial kidneys by filling them with an aqueous solution of formaldehyde which is relatively concentrated, and usually has a concentration of 1 to 5%, and ship them in the sterilized state. Prior to use for dialysis, the users remove the formaldehyde by washing, warm the artificial kidneys to the body temperature, and perform other necessary treatments (for example, fill a physiological saline solution containing heparin into the blood-flowing section of the artificial kidneys). This method permits effective sterilization. However, since the formaldehyde used as a sterilizing agent is toxic to man, it must be completely removed from the artificial kidneys. This requires the flowing of a great quantity of water for a long period of time. Such a washing operation is troublesome, and the users must spend considerable labor and time. There is an additional defect that if washing is stopped after the formaldehyde concentration in the washing effluent has decreased and no substantial formaldehyde is detected, the formaldehyde remaining in the hollow filaments gradually oozes out of the filaments.

According to the other method, the manufacturers sterilize the artificial kidneys by passing a gaseous mixture, consisting of 10 to 30% ethylene oxide or propylene oxide as a sterilizing ingredient and the remainder being Freon ® or $CO_2$ as a carrier ingredient, into the artificial kidneys in the dried state, and ship them in the sterilized condition. Prior to use, the users perform necessary treatments on the dried sterilized artificial kidneys; for example, they fill them with a dialyzate and an isotonic saline solution. This method has the defect that gases such as ethylene oxide or propylene oxide are adsorbed by the hollow filaments, and the gases remaining in the filaments react with chlorine ions in the physiological saline solution to form a toxic chlorohydrin compound. Washing of these residual gases require the passing of a physiological saline solution in an amount of as large as more than 2 liters. Furthermore, since the hollow filaments of the artificial kidneys are capillary tubes, in order to remove the bubbles completely, the washing liquid must be passed for longer periods of time, or the washing liquid must be passed after replacing the air in the hollow filaments by aseptic carbon dioxide gas. In the latter case, the users require various devices such as a carbon dioxide gas cylinder, a sterilizing filter, a pressure control device, or a flow rate controlling device. If the bubbles remain in the hollow filaments, minute bubbles are very likely to flow into the body during dialysis, or may cause coagulation of the blood within the hollow filaments, thus increasing the amount of the blood remaining in the dialyzer afer dialysis, and also losses of the blood.

Furthermore, since by the gas sterilizing method, artificial kidneys in the dried state are rendered wet by pretreatment, the performance of the artificial kidneys tends to change, and has poor reproducibility.

A third sterilizing method suggested involves applying gamma-rays in a dose of 0.5 to 5 Mrads to artificial kidneys. This radiation sterilizing method is free from a problem of residual toxicity, but, as in the second method, tends to cause changes in the performance of the artificial kidneys in pretreatments, such as the filling of a physiological saline solution and a dialyzate into the artificial kidneys in the dried state. In addition, the materials which constitute the artificial kidneys are susceptible to degradation by application of ionizing radiation, and problems are still left unsolved in the improvement and choice of materials.

Generally, sterilization also includes heat sterilization which is widely practised for the sterilization of injection syringes and instruments for surgical operation. For example, Japanese Pharmacopoeia, the 9th revised edition, sets forth a method for controlling microorganisms by a high-pressure steam sterilizing method which comprises heating the material to be sterilized in saturated steam at 115° C. for 30 minutes, at 121° C. for 20 minutes, or at 126° C. for 15 minutes. The Japanese Pharmacopoeia also permits the use of an intermittent sterilizing method which comprises heating the material to be sterilized for 30 to 60 minutes in water or flowing steam at 80° to 100° C. every 24 hours, and repeating this heating operation 3 to 5 times.

Since heat sterilization is advantageous because of the freedom from residual toxicity and the ease of washing, it would be very convenient if this method can be applied to artificial kidneys. In fact, the heat sterilizing method has never been applied to artificial kidneys, and no attempt at it has been made because it has been considered as quite impossible to heat sterilize artificial kidneys filled with a primer. The reason for this is that upon heating, the artificial kidneys undergo deformation, cracking or breakage owing to the thermal expansion of the primer and the air contained in the artificial kidneys and the generation of the autogenous pressure of steam, and consequently, leakage of the primer occurs, and also, it is difficult to seal artificial kidneys aseptically after sterilization.

The present invention has successfully solved the above problems.

It is an object of this invention to provide a method for heat sterilizing artificial kidneys filled with a primer.

Another object of this invention is to supply to the users artificial kidneys which do not substantially require pretreatment.

SUMMARY OF THE INVENTION

According to the present invention, there is provided a method for heat sterilizing an artificial kidney comprising a receptacle having accommodated therein permselective hollow filaments and including inlet and outlet ports for the blood and inlet and outlet ports for a dialyzate, which comprises (a) filling a primer consisting of water or a water solution into the artificial kidney, (b) connecting a pressure buffer tank to at least one of the inlet and outlet ports, (c) sealing the remaining ports by stopper means, (d) heating the artificial kidney to a temperature of 80° to 130° C. to heat sterilize it, and moving the gas and a part of the primer in the artificial kidney, which have been expanded by heating, to the pressure buffer tank, (e) cooling the artificial kidney to return the primer in the buffer tank to the artificial kidney, and (f) aseptically sealing the port connected to the pressure buffer tank.

BRIEF DESCRIPTION OF THE ACCOMPANYING DRAWINGS

FIGS. 8 and 9 show connecting tubes suitable for use in the method shown in FIG. 7, FIGS 8(a) and 9(a) being longitudinal sectional view, and FIGS. 8(b) and 9(b) being cross-sectional views taken along the line A-A'.

DETAILED DESCRIPTION OF THE INVENTION

The important feature of the heat sterilization method of this invention is that a pressure buffer tank having a special function is connected to at least one of the inlet and outlet ports for the blood and inlet and outlet ports for the dialyzate of an artificial kidney filled with a primer and the remaining ports are sealed, and in this condition, the artificial kidney is heated to a temperature of 80° to 130° C. Heating under these conditions results in the movement of primer and gases such as air present in the artificial kidney, which are expanded by the rise in temperature, to the pressure buffer tank. As a result, the internal pressure of the artificial kidney which is caused by the thermal expansion of fluids (the primer and gases) and the increase of the steam pressure is reduced, and the deformation, cracking or breakage of the artificial kidney which would occur in the absence of such a buffer action can be avoided effectively.

Thus, the pressure buffer tank used in this invention has a dual function of storing expanded fluids (primer and gases) in the artificial kidney, and of checking the increase of the pressure within the artificial kidney which occurs at the time of heating.

The pressure buffer tank used in the method of this invention may be a tank which communicates with the outer atmosphere in regard to pressure but is aseptically shielded from the outer atmosphere, or a tank which is shielded from the outer atmosphere both in regard to pressure and microbes (for example, a closed bag). When a closed bag is used, it is preferably one which can expand itself according to the movement of the expanded fluids (primer and gases) inside so that it can exhibit a pressure buffer action.

When the connection of the artificial kidney and the pressure buffer tank is released after the heat sterilization of the artificial kidney by the method of this invention, the port connected to the pressure buffer tank should be sealed by a means for preventing the leakage of the primer. According to the method of this invention, it is easy to perform this sealing aseptically. This is another important feature of the invention.

In the present invention, heat sterilization is carried out preferably in accordance with the Japanese Pharmacopoeia, the 9th revised edition. The heat sterilization is carried out at a temperature of 80° to 130° C. since the high-pressure steam sterilization method (115° to 120° C.) and the intermittent sterilization method (80° to 100° C.) are applied.

The invention is specifically described below with reference to the accompanying drawings.

Figure 1:
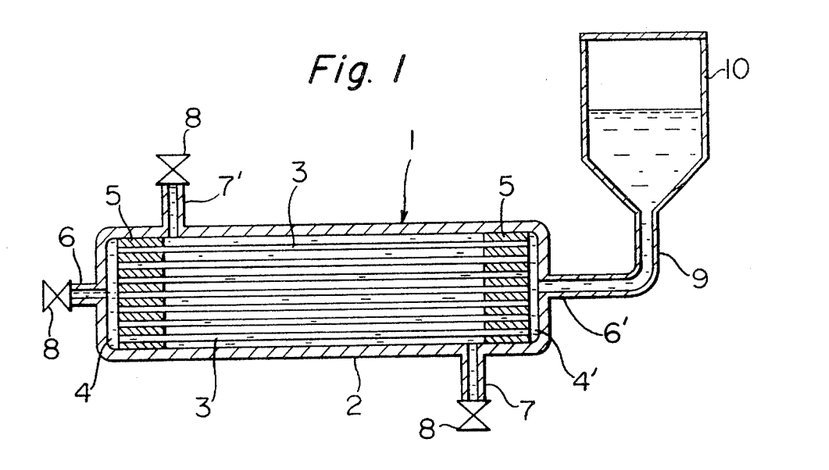
FIG. 1 is a schematic view showing the performance of the method of heat sterilization in accordance with this invention.

Referring to FIG. 1 which schematically shows the heat sterilization of an artificial kidney by the method of this invention, an artificial kidney 1 comprises a receptacle 2 having accommodated therein a number of permselective hollow filaments 3. A pair of partition walls 5 are provided within the receptacle 2 to support the hollow filaments 3. The receptacle 2 includes a blood inlet port 6 and a blood outlet port 6' both composed of a normally narrow by-pass tube having an opening, and a dialyzate inlet port 7 and a dialyzate outlet port 7' both composed of a normally thick by-pass tube having an opening. One end of the receptacle 2 is a blood distributing section 4 and the other end is a blood gathering section 4', which are both separated by the partition walls 5 from a centrally located chamber for dialysis in the receptacle 2. The receptacle 2, the hollow filaments 3, the partition walls 5, and the by-pass tubes 6, 6', 7 and 7' are made of materials which do not substantially deform by heat at a temperature of 80° to 130° C. employed for heat sterilization.

In performing the heat sterilization of the artificial kidney 1 in accordance with the method of this invention, a primer composed of water or a water solution is filled in the artificial kidney 1. As a result, the primer fills the entire spaces of receptacle 2, i.e. the spaces in the hollow filaments which are passages for the blood, the spaces among the hollow filaments which are passages for the dialyzate, the spaces inside the blood distribution section 4 and the blood gathering section 4', and the spaces within the by-pass tubes 6, 6', 7, 7'. At least one (by-pass tube 6' in FIG. 1) of the by-pass tubes 6, 6', 7, 7' is connected to a pressure buffer tank 10 through a conduit 9, and the other by-pass tubes are sealed to prevent leakage of the primer (for example, by using stoppers or by weld sealing). In this condition, the artificial kidney 1 is heated to a temperature of 80° to 130° C. to heat sterilize it. At this time, the pressure buffer tank 10 may be heated together with the artificial kidney 1. Or the pressure buffer tank 10 may be disposed outside the heater, to heat only the artificial kidney 1. When the artificial kidney 1 is heat-sterilized, the expansion of the primer and the air in the artificial kidney by the rise in temperature and the autogenous pressure of steam cause the expanded portions of these fluids to go out of the artificial kidney 1 and move to the pressure buffer tank 10. As a result, the pressure within the artificial kidney can be buffered.

Cooling of the artificial kidney after the end of sterilization causes the fluids remaining in it to shrink, and reduces the pressure of steam. Hence, the inside of the artificial kidney is under reduced pressure. As a result, the artificial kidney tends to return to the normal atmospheric pressure from the reduced pressure, and the water or aqueous solution stored in the pressure buffer tank 10 flows into the artificial kidney 1 through the conduit 9.

The heat sterilization method of this invention can be performed by either of the two embodiments described hereinbelow.

Figure 2:
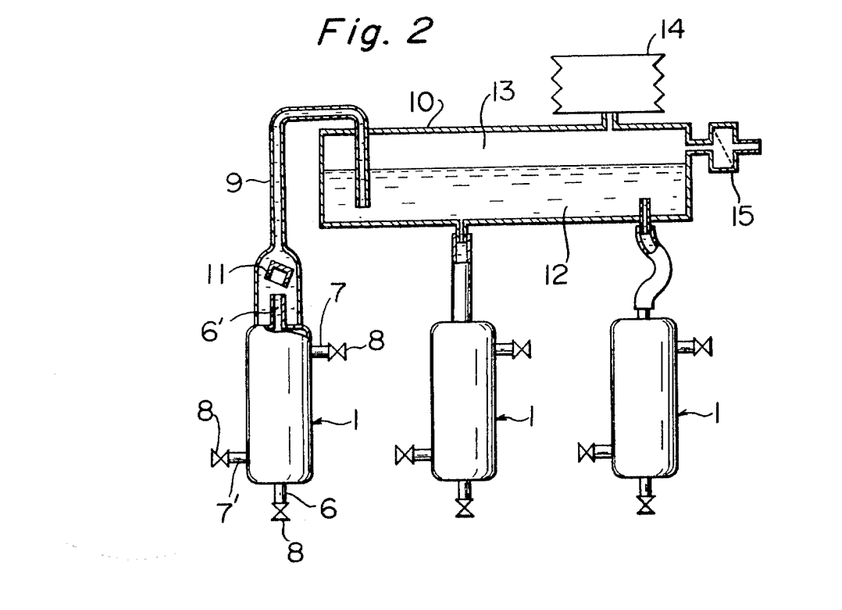
FIG. 2 is a view showing one embodiment of the heat sterilizing method of this invention.

According to one embodiment, a pressure buffer tank having a primer therein is used, and is connected to the artificial kidney so that the primer in the artificial kidney communicates with the primer in the pressure buffer tank, prior to performing the heat sterilization. FIG. 2 shows this embodiment. Referring to FIG. 2, a plurality of artificial kidneys 1 are connected to one pressure buffer tank 10, and the primer in each of the artificial kidneys communicates with a primer phase 12 of the pressure buffer tank 10. A gaseous phase 13 is present over the liquid phase 12. The reference numeral 14 represents a bellows for pressure buffering, and the reference numeral 15, a sterilizing filter. Preferably, the pressure buffering is carried out by using one or both of the bellows and the sterilizing filter. In this first embodiment, the fluids (primer and air) expanded during heat sterilization move from the artificial kidney to the pressure buffer tank 10. On cooling, only the primer returns to the artificial kidney 1, and the air remains in the gaseous phase 13 and never returns. Thus, the amount of a gaseous ingredient such as air present in the artificial kidney decreases correspondingly after the heat sterilization treatment.

The amount of the gaseous ingredient present in the artificial kidney is desirably as small as possible, and therefore, the decrease of the amount of the gaseous ingredient brought about by the heat sterilization treatment is advantageous. In the present application, the decrease of the content of such a gaseous ingredient is sometimes referred to as the "improvement of the primed condition of an artificial kidney." When the filled condition of the artificial kidney is insufficient, the bubbles present in the path of blood may induce coagulation and other undesirable phenomena. The bubbles present in the bath of dialyzate reduce both the available membrane area of the hollow filaments and the dialyzing efficiency. The first embodiment of the method of the present invention is very preferable because it can achieve this improvement of the primed condition of artificial kidneys. In the first embodiment, the pressure buffer tank 10 is made of such a material as metals, glass and thermally stable resins, and the conduit 9 is made preferably of such a material as a silicone rubber or a thermally stable synthetic rubber.

Figure 3:
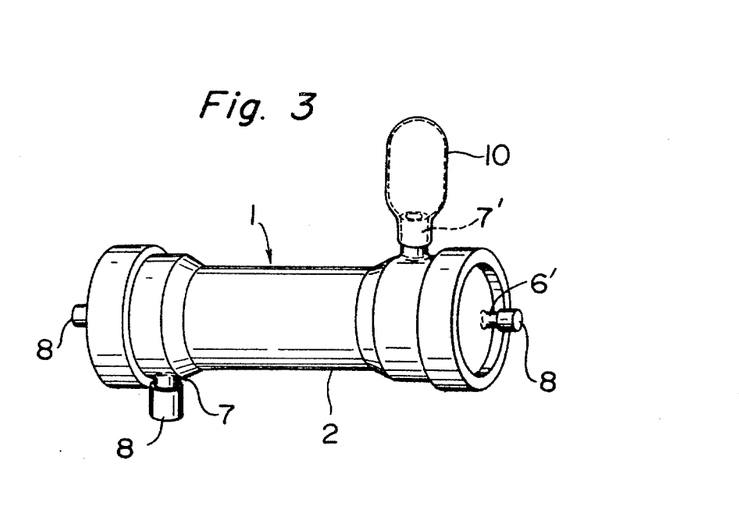
FIG. 3 is a view showing another embodiment of the heat sterilizing method of this invention.

A second embodiment of the method of this invention involves using a pressure buffer tank not including a primer and therefore occupied only with a gas phase, and connecting to at least one of the by-pass tubes of the artificial kidney, prior to heat sterilization. FIG. 3 shows one example of the second embodiment, and pressure buffer tank 10 shaped like a balloon is connected to a by-pass tube 7' of the artificial kidney. According to this method, the fluids within the artificial kidney which have been expanded by heat sterilization are absorbed by the expansion of the pressure buffer tank (buffer bag) itself. As a result, the pressure is reduced, and the load on the receptacle, the blood distributing section and the blood gathering section of the artifical kidney becomes small. The improvement of the primed condition cannot be achieved by the second embodiment.

The material for the buffer bag is required to have the property of not breaking upon expansion, wet heat resistance at 80° and 130° C., and safety and nontoxicity for medical uses. Examples are natural rubbers, synthetic rubbers such as polyisoprene rubber or polybutadiene rubber, silicone rubbers, and rubbery elastomers such as polyurethane elastomers, or materials not having rubbery elasticity such as polypropylene, polyesters, nylon, and polypropylene/polyester laminate films. The volume of the buffer bag is such that its maximum volume on expansion within the limit of pressure is at least larger than the increase in the volume of fluids (primer and air) in the artificial kidney which is ascribable to heat expansion.

Figure 4:
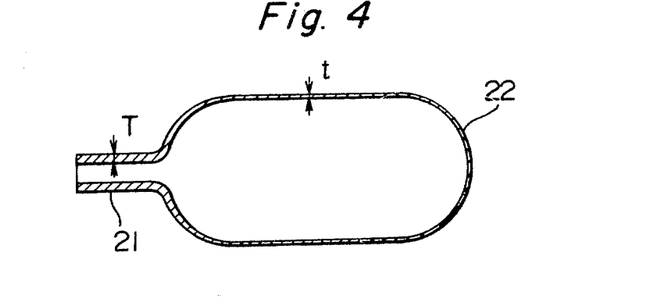
FIGS. 4 to 6 show typical examples of a buffer bag used in the embodiment shown in FIG. 3.
Figure 5:
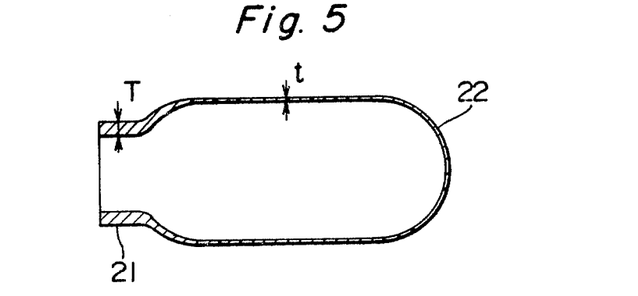
Figure 6:
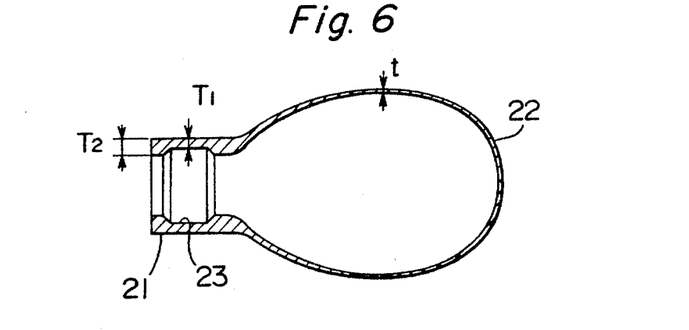

The buffer bag used in the second embodiment may be of various shapes such as a bag-like, balloon-like or tubular shape. An especially preferred buffer bag is a bag having an internal structure of a thick portion 21 and a thin portion 22, as shown in FIGS. 4 to 6. The thick portion is a neck portion to be fitted to a by-pass tube of the artificial kidney, and the thin portion is an expansible portion. The thickness (T mm) of the thick portion and the thickness (t mm) of the thin portion have the relation shown by the following equations (1) to (3).

$$0.05 \text{ mm} \leq t \leq 2.0 \text{ mm} \tag{1}$$

$$0.25 \text{ mm} \leq T \leq 5.0 \text{ mm} \tag{2}$$

$$1 < T/t \leq 30 \tag{3}$$

The volume of the buffer bag under zero gauge pressure (atmospheric pressure) is usually 2 to 100 ml, preferably 4 to 50 ml. The maximum volume on expansion of the bag differs according to the type of the artificial kidney and the amount of a primer filled in it. For example, when the amount of the primer filled in the artificial kidney is 400 ml and the amount of residual air is 0 to 20 ml, the fluids are expected to increase by an amount of 20 to 70 ml upon expansion. Hence, the buffer bag is expansible when its volume at zero gauge pressure is less than its maximum volume on expansion. Preferably, at the time of connecting the buffer bag, it is flattened, or is filled with a small amount of water or a water solution so as to admit no gas into it. The thin portion of the bag should have a thickness of usually 0.05 to 2.0 mm, preferably 0.10 to 1.0 mm, so that the bag can be expanded and flattened. When it is necessary to expand the bag, it should have a break elongation of preferably 100 to 1500%, more preferably 300 to 1000%.

The neck portion of the bag to be secured to a by-pass tube of the artificial kidney is a fixing part of the bag, and is thick so as to provide a sealing action for the prevention of leakage of the primer, etc. and contamination after heat sterilization. The thickness (T) is usually 0.25 to 5.0 mm, preferably 0.4 to 3.0 mm. The thick portion and the thin portion are usually fabricated into a unitary structure. Alternatively, they may be separately fabricated, and formed into a unitary structure by, for example, bonding. The thicknesses of these two portions should satisfy the equation (3) given hereinabove.

FIG. 4 shows a buffer bag suitable for connection to a thin by-pass tube of the artificial kidney, for example, a blood inlet or oulet port. The inside diameter and length of the neck portion 21 to be connected to the by-pass tube should preferably be of magnitudes which permit engagement with the by-pass tube.

FIG. 5 shows a buffer bag suitable for connection to a thick by-pass tube of the artificial kidney, for example, a dialyzate inlet or oulet port.

FIG. 6 shows a buffer bag in which the inside surface of the neck portion conforms to the outer shape of a by-pass tube. In this case, the thickness T of the thick portion is an average of the minimum thickness $T_1$ and the maximum thickness $T_2$.

The shape of the expanded portion 22 may be substantially cylindrical or elliptic, or may be generally oval as shown in FIG. 6.

According to the method of this invention, the openings connected to the pressure buffer tank should be aseptically sealed before the connection between the artificial kidney and the pressure buffer tank is released after the heat treatment. The following two major methods are available for achieving the aseptic sealing.

A first method comprises connecting a conduit 9 with a thicker tip portion to a by-psss tube 6' of an artificial kidney 1 as shown at the left end of FIG. 2, suspending a stopper 11 for preventing leakage of a primer in the thicker portion of the conduit 9, and fitting the stopper 11 into the by-pass tube 6' after the end of the heat sterilization treatment and before disconnecting the by-pass tube 6' and the conduit 9. Since after heat sterilization, the inside of the artificial kidney and the inside of the pressure buffer tank are microbe-free, the above operation can achieve an aseptic sealing of the by-pass tube 6'.

Figure 7:
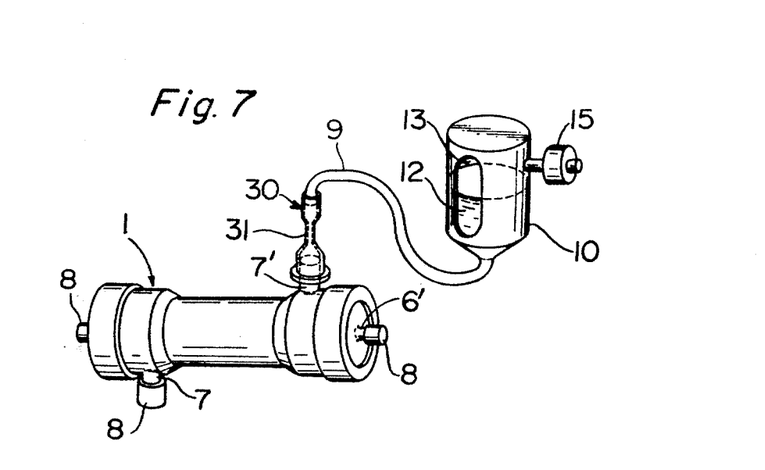
FIG. 7 is a view showing one method for aseptic sealing in the method of this invention.

A second method comprises connecting a by-pass tube 7' and a conduit 9 through a connecting tube 30 having a weld-sealable part 31 as shown in FIG. 7, and welding the weld-sealable part 31 after the heat sterilization treatment and before the disconnection of the by-pass tube 7' and the conduit 9 thereby to achieve an aseptic sealing. The connecting tube 30 may be made of any material which can be sterilized in high pressure steam and can be welded at the weld-sealable part 31 by heat, high frequency or ultrasonic waves. Examples are polyvinyl chloride, polyolefins, and polyurethane.

When the by-pass tubes of the artificial kidney or the conduit 9 are weld-sealable, the aseptic sealing may be achieved by weld-sealing these portions. When the aforesaid pressure buffer bags are used, they may be used as a seal without separation after heat sterilization.

Figure 8A:
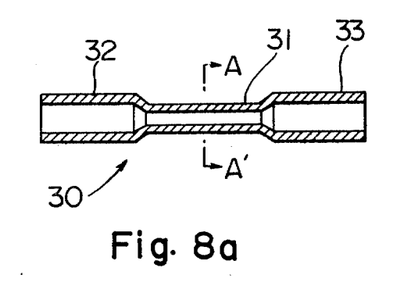
Figure 8B:
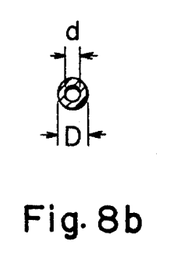
Figure 9A:
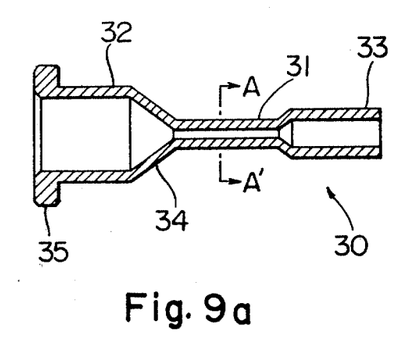
Figure 9B:
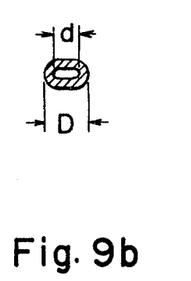

The connecting tube suitable for use in the second method is a cylindrical tube composed of a cylindrical connecting part 32, a weld-sealable part 31 and a cylindrical conduit part 33, as shown in FIGS. 8 and 9. The weld-sealabe part 31 is a thin neck-like structure having a maximum outside sectional dimension of 2 to 15 mm, and a maximum inside sectional dimension of 1 to 14 mm, and is made of a material which can be welded. The weld-sealable part 31 is centrally located in the connecting tube 30, and the connecting part 32 and the conduit part 33 are located at the ends of the connecting tube 30.

The shapes and dimensions of the connecting part 32 and the conduit part 33 are determined in consideration of the shape and sealability of a tube to be connected. The weld-sealable part 31 preferably has an inside sectional size of at least 1 mm from the viewpoint of serviceability as a conduit. Preferably, its upper limit is 14 mm in view of the size of the by-pass tubes of the artificial kidney and the area to be welded. The maximum outside dimension of the weld-sealable part 31 is preferably 2 to 15 mm so as to hold an aqueous solution and the area to be welded. More preferably, the weld-sealable part 31 has a maximum outside sectional dimension of 3 to 8 mm and an inside sectional dimension of 2 to 7 mm. The sectional shape of the connecting tube may be circular, elliptical, oval or rectangular. If the weld-sealable part 31 is of a fine diameter, its sectional shape is preferably circular for ease of a welding operation. If it is of a relatively large diameter, the sectional shape is preferably a flattened ellipse, an oval shape or a rectangle for the same reason. However, the shape is not limited to these examples.

FIG. 8 shows a connecting tube 30 suitable for connection to a thin by-pass tube (a blood inlet or oulet port) of the artificial kidney. The connecting part 32 and the conduit part 33 are of cylindrical shape in order to achieve fitting and sealing. The section taken along the line A—A' of the weld-sealable part 31 is circular.

FIG. 9 shows a connecting tube suitable for connection to a thick by-pass tube (a dialyzate inlet or outlet port) of the artificial kidney. The shape of the connecting part 32 is a cylinder having a conical top 34. A collar 35 is provided in the tube 30 so as to achieve fitting and sealing with the by-pass tube and facilitate the operation of removing the connecting tube at the time of using the artificial kidney in patients. In this connecting tube, the A–A' section of the weld-sealable port 31 is a flattened oval shape.

According to the method of this invention, artificial kidneys can be easily heat sterilized. The heat sterilization treatment does not cause breakage or deformation of the artificial kidneys filled with water or a water solution, or a poor seal. Furthermore, the flow paths of the blood can be maintained in an operable condition. In addition, the artificial kidneys after heat sterilization can be aseptically sealed to prevent secondary microbial contamination.

Furthermore, the artificial kidneys heat sterilized by the method of this invention are improved in their primed condition, and can exhibit excellent substance exchange performance and affinity for the blood. The artificial kineys heat sterilized by the method of this invention, as a whole, have a high level of assurance of the freedom from microbes, are free from residual toxicity and can be easily washed for use.

According to another aspect of this invention, there is provided an artificial kidney suitable for heat sterilization which consists essentially of a receptacle, hollow filaments accommodated therein and partition walls supporting the hollow filaments in place, wherein the hollow filaments, the partition walls and the receptacle have substantial thermal stability at a temperature within the range of 40° to 130° C., and the coefficient of linear expansion ($A[1/°C.]$) of the partition walls, at a temperature within the range of 40° to 130° C., has the following relation to the coefficient of linear expansion ($B[1/°C.]$) of the receptacle and the temperature ($\theta[°C.]$)

$$4.13 \times 10^{-5} \exp(0.00769\theta) \leq A \leq 2B$$

and the partition walls do not have a second order transition point between 50° and 120° C.

The artificial kidney having the above structure does not undergo deformation, breakage or poor sealing by heat sterilization, and the blood flow paths and the dialyzate flow paths can be maintained in good condition. As a result, the artificial kidney can exhibit superior performance owing also to the thermal stability of the hollow filaments.

The artificial kidneys which meet the above conditions can be constructed by a method known per se using the following materials.

Examples of the materials for the hollow filaments are cellulose, cellulose esters, polyacrylonitrile, polyvinyl alcohol, poly(aromatic amides) such as polyamide-benzohydrazide, isophthalamide, polycarbonate, polysulfones and polyethers. Of these, cellulose and polyacrylonitrile are especially preferred.

The material for the receptacle may, for example, be polycarbonate, poly(4-methylpentene-1), polyvinylidene fluoride and polyacetal. The polycarbonate and poly(4-methylpentene-1) which have a high level of transparency are especially preferred materials.

High-molecular-weight polymers are preferred as materials for the partition walls. Preferred polymers are those which are obtained by addition polymerization and cross-linking from at least one prepolymer and a curing agent, etc. without any substantial change in total amounts of the reactants before and after the reaction. Specific examples of such polymers are urethane resins and epoxy resins. In particular, poly(ester-type urethanes) obtained by addition polymerization of (I) an isocyanatoterminated prepolymer and (II) a polyol derived from a hydroxy-containing fatty acid and a glycerin ester are preferred.

The following examples illustrate the present invention in more detail.

EXAMPLE 1 AND COMPARATIVE EXAMPLE 1

A bundle of 10,000 cellulosic hollow filaments having an inside diameter of 250 microns and a membrane thickness of 30 microns was accommodated in a polycarbonate receptacle. Both ends of the bundle were fixed by a urethane resin to form partition walls. A blood distributing plate made of polypropylene was fixed by clamping with a bag cap of polycarbonate.

The blood-flowing section and the dialyzate flowing section of the resulting artificial kidney containing hollow filaments were filled with distilled water. A silicone rubber tube was connected to one opening for the dialyzate and the other opening of the tube was connected to 200 ml of distilled water placed in a glass pressure buffer tank. Using a high-pressure steam sterilizing machine, the artificial kidney was heat sterilized at 115° C. for 30 minutes, cooled gradually to room temperature, and withdrawn from the sterilizer.

The weight (a) of the resulting artificial kidney before priming, its weight (b) after priming, and its weight (c) after heat sterilization were measured, and from these values, the amounts of a primer before and after heat sterilization were calculated. The results are shown in Table 1.

For comparison (Comparative Example 1), in order to improve the primed condition, the blood flowing section and the dialyzate flowing section of the artificial kidney were first purged with carbon dioxide gas, and then filled with distilled water. The results obtained are also shown in Table 1. It is seen from the results that the heat sterilized artificial kidney obtained by this invention showed improvement both in the substantial amount of the primer and in appearance.

Table 1

| | (Unit of weight: g) | |
|---|---|---|
| Items | Example 1 | Comparative Example 1 |
| Weight (a) before priming | 422 | 422 |
| Weight (b) after priming | 844 | 853 |
| Amount (b-a) of primer before heat sterilization | 422 | 431 |
| Weight (c) after heat sterilization | 862 | — |
| Amount (c-a) of primer after heat sterilization | 440 | |
| Primed condition | No bubbles were seen, and the primed condition was very uniform. | Small bubbles were observed. |

The artificial kidney obtained was subjected to a sterility test. Negative results were obtained both in regard to Schizomycetes and Eumycetes. It was also confirmed that no leak occurs in the hollow filaments in the artificial kidney. Then, it was examined for dialyzing performance.

At this time, in order to confirm the effect of the improvement of the primed condition, the dialyzing performance was measured in the primed condition of the present invention. Then, the primer in the dialyzate-flowing section was pulled out in an amount of 10 g, 20 g, and 30 g, respectively, and the artificial kidney was well shaken to decrease the size of the bubbles and render their distribution uniform. Then, the urea dialyzing performance of the artificial kidney was measured.

The results are shown in Table 2.

Table 2

| | Amount of the primer withdrawn (g) | Dialyzing performance (ml/min.) |
|---|---|---|
| Example 1 | 8 | 176 |
| Comparative Example 1 | 10 | 171 |
| | 20 | 163 |
| | 30 | 154 |

The results of Table 2 demonstrate that the primed condition affects the dialyzing performance.

EXAMPLES 2 to 4

Hollow filament-containing artificial kidneys constructed under the same conditions as in Example 1 and filled with distilled water were heat sterilized in the same way as in Example 1 at varying temperatures.

The weights of each of these artificial kidneys before and after priming (a and b) and its amount after heat sterilization (c) were measured, and from these values, the amounts of the primer in each artificial kidney before and after heat sterilization were calculated. The results are shown in Table 3.

The artificial kidneys so heat-sterilized were subjected to a sterility test, and it was found that negative results were obtained both in regard to Schizomycetes and Eumycetes.

The results show that the present invention can afford artificial kidneys having improved primed conditions.

Table 3

| Items | Example 2 | Example 3 | Example 4 |
|---|---|---|---|
| Sterilizing temperature (°C.) | 80 | 121 | 126 |
| Sterilizing time (minutes) | 120 (5 times) | 20 | 15 |
| Sterilizing pressure (kg/cm$^2$) | 1.0 | 2.2 | 2.6 |
| Weight before priming (a) (g) | 425 | 420 | 423 |
| Weight after priming (b) (g) | 846 | 843 | 845 |
| Amount of the primer before heat sterilization (b-a) (g) | 421 | 423 | 422 |
| Weight after heat sterilization (c) (g) | 859 | 862 | 862 |
| Amount of the primer after priming (c-a) (g) | 434 | 442 | 439 |
| Primed condition | Scarcely any bubbles | No bubbles | No bubbles |

EXAMPLE 5

A hollow filament-containing artificial kidney was constructed in the same way as in Example 1. The blood flowing section and the dialyzate flowing section of the artificial kidney were filled with distilled water at 20° C. A silicone rubber buffer bag of the type shown in FIG. 6 and having a capacity of 50 ml with the thickness of the thin portion being 0.5 mm was fitted to one opening for the dialyzate with care taken not to admit air into the bag. The amount of the water filled in the artificial kidney was 422 ml, and the amount of the residual air was 17 ml when measured after the heat sterilization. Two openings for the blood and one opening for the dialyzate were sealed by silicone rubber stoppers to prevent leakage of the filled liquid.

The artificial kidney to which the buffer bag had been secured was heat sterilized at 115° C. and 2.0 kg/cm$^2$ for 30 minutes using a high-pressure steam sterilizer. The pressure of the inside of the sterilizer was maintained at 2.0 kg/cm$^2$ by the introduction of microbe-free air, and the artificial kidney was cooled slowly down to room temperature and withdrawn from the sterilizer.

There was no difference between the weights of the artificial kidney before and after the heat sterilization. No leakage of the filled liquid occurred. A sterility test on the artificial kidney showed negative results both in regard to Schizomycetes and Eumycetes. It was also found that there was no leak in the hollow filaments in the artificial kidney.

EXAMPLES 6 TO 12 AND COMPARATIVE EXAMPLES 2 TO 4

Hollow filament-containing artificial kidneys were constructed in the same way as in Example 5. The blood flowing section and the dialyzate flowing section of each of the artificial kidneys were filled with distilled water kept at 20° C. A buffer bag was secured to one opening for the dialyzate with care taken not to admit air into it. Each of the artificial kidneys was heat sterilized under the various conditions shown in Table 4. The results are shown in Table 4.

A sterility test performed on the artificial kidneys in Examples 6 to 12 showed negative results.

The silicone rubber buffer bags were expansible balloon-like bags as shown in FIGS. 5 and 6. The polypropylene buffer bags were made of polypropylene films.

The breakage of the buffer bags used in Comparative Examples 2 to 4 as shown in Table 4 was presumably because the volume of each buffer bag was smaller than the increase of the volume of water and remaining air in the artificial kidney which was caused by heat expansion.

Table 4

| Example (Ex.) or Comparative Example (CE.) | Sterilizing temperature (°C.) | Sterilizing time (min.) | Sterilizing pressure (kg/cm$^2$) | Buffer bag Volume (ml)*1 | Buffer bag Material | Buffer bag Thickness | Amount of primer (ml) | Amount of residual air (ml) | Results Breakage of the buffer bag | Results Coming off of the stopper |
|---|---|---|---|---|---|---|---|---|---|---|
| Ex. 6 | 115 | 30 | 2.0 | 30 | Silicone rubber | 0.5 | 424 | 17 | No | No |
| Ex. 7 | 121 | 20 | 2.2 | 30 | " | 0.5 | 432 | 8 | No | No |
| Ex. 8 | 126 | 15 | 2.6 | 40 | " | 0.5 | 445 | 1 | No | No |
| Ex. 9 | 80 | 120 (5 times) | 1.0 | 20 | Polypro- | 0.2 | 420 | 20 | No | No |
| Ex. 10 | 100 | 60 (3 times) | 1.2 | 30 | " | 0.2 | 422 | 18 | No | No |
| Ex. 11 | 115 | 30 | 2.0 | 100 | " | 0.2 | 447 | 0 | No | No |
| Ex. 12 | 126 | 15 | 2.6 | 30 | Silicone rubber | 0.7 | 445 | 1 | No | No |
| CE. 2 | 115 | 30 | 2.0 | 10 | Polypropylene | 0.2 | 422 | 17 | Yes | No |
| CE. 3 | 121 | 20 | 2.2 | 20 | " | 0.2 | 434 | 9 | Yes | No |
| CE. 4 | 126 | 10 | 2.6 | 20 | Silicone rubber | 0.2 | 446 | 0 | Yes | No |

*1Maximum volume within the limit of pressure.

EXAMPLE 13

A hollow filament-containing artificial kidney constructed in the same way as in Example 1 was filled with a 15% by weight aqueous solution of sodium chloride, and a polyvinyl chloride connecting tube for medical use having the shape shown in FIG. 9 was fitted to an opening for a dialyzate and disposed as shown in FIG. 7. A sterilizing filter was secured to the buffer tank, and the artificial kidney was sterilized at 115° C. for 30 minutes. The artificial kidney was cooled, and the seal-weld portion of the connecting tube was welded by an ultrasonic welder to shield the artificial kidney aseptically from the buffer means. Then, the conduit part of the connecting tube was cut off to provide a heat sterilized artificial kidney.

A sterility test on the product showed that the results were negative both in regard to Schizomycetes and Eumycetes.

What we claim is:

1. A method for heat sterilizing an artificial kidney comprising a receptacle having accommodated therein permselective hollow filaments and including inlet and outlet ports for the blood and inlet and outlet ports for a dialyzate, which comprises
   (a) filling a primer consisting of water or a water solution into the artificial kidney,
   (b) connecting a pressure buffer tank to at least one of the inlet and outlet ports, a conduit being provided between said at least one port and the pressure buffer tank, one end of the conduit being connected to said at least one port and the other end of the conduit being connected to the pressure buffer tank thereby to connect said at least one port to the pressure buffer tank,
   (c) sealing the remaining ports by stopper means,
   (d) heating the artificial kidney to a temperature of 80° to 130° C. to heat sterilize it, and moving gas and a part of the primer in the artificial kidney, which have been expanded by the heating, to the pressure buffer tank,
   (e) cooling the artificial kidney to return the primer in the buffer tank to the artificial kidney, and
   (f) aseptically sealing the port connected to the pressure buffer tank.

2. The method of claim 1 wherein after the end of step (f), the connection provided in step (b) is released.

3. The method of claim 1 wherein prior to step (b), the primer is introduced into the pressure buffer tank to form a phase of the primer and a gaseous phase in the pressure buffer tank, and then the connection in step (b) is performed, thereby achieving communication of the primer in the artificial kidney with the primer phase in the buffer tank.

4. The method of claim 3 wherein the pressure buffer tank communicates with the outside atmosphere in regard to pressure, and is shielded aseptically from the outside atmosphere.

5. The method of claim 1, which further comprises providing a continuous cylindrical tube, having a cylindrical connecting part at one end, a centrally located weld-sealable part and a cylindrical conduit part at the other end, between said at least one port and the said one end of the conduit, fitting said connecting part to said at least one port, and fitting said conduit part to said one end of the conduit.

6. The method of claim 5 wherein the aseptic sealing of step (f) is performed by welding the weld-sealable part.

7. The method of claim 6 wherein the outside diameter of the weld-sealable part is made smaller than the outside diameter of the connecting part and the outside diameter of the conduit part, and the cross-section of the weld-sealable part is formed to have a maximum outside dimension of 2 to 15 mm and a maximum inside dimension of 1 to 14 mm.

8. A method for heat sterilizing an artificial kidney comprising a receptacle having accommodated therein permselective hollow filaments and including inlet and outlet ports for the blood and inlet and outlet ports for a dialyzate, which comprises
   (a) filling a primer consisting of water or a water solution into the artificial kidney,
   (b) connecting a pressure buffer tank to at least one of the inlet and outlet ports, said pressure buffer tank being a closed bag made of a material having rubbery elasticity so that it is expansible by an increase in internal pressure, said bag being formed as an integrated structure of a thick portion and a thin portion, said thick portion being a neck portion which is to fit an inlet or outlet port of the artificial kidney and the thin portion being an expansible portion, and the thickness (T mm) of the thick portion and the thickness (t mm) of the thin portion having the relation shown by the following equations (1) to (3):

$$0.05 \text{ mm} \leq t \leq 2 \text{ mm} \quad (1)$$

$$0.25 \text{ mm} \leq T \leq 5 \text{ mm} \quad (2)$$

$$1 < T/t \leq 30 \quad (3),$$

(c) sealing the remaining ports by stopper means,
   (d) heating the artificial kidney to a temperature of 80° to 130° C. to heat sterilize it, and moving gas and a part of the primer in the artificial kidney, which have been expanded by the heating, to the pressure buffer tank,
   (e) cooling the artificial kidney to return the primer in the buffer tank to the artificial kidney, and
   (f) aseptically sealing the port connected to the pressure buffer tank.

9. The method of claim 8 wherein after the end of step (f), the connection provided in step (b) is released.

10. The method of claim 8 wherein prior to step (b), the primer is introduced into the pressure buffer tank to form a phase of the primer and a gaseous phase in the pressure buffer tank, and then the connection in step (b) is performed, thereby achieving communication of the primer in the artificial kidney with the primer phase in the buffer tank.

* * * * *